(12) United States Patent
Wu et al.

(10) Patent No.: US 11,517,253 B2
(45) Date of Patent: Dec. 6, 2022

(54) DEVICE AND METHOD FOR LIVENESS DETECTION

(71) Applicant: FaceHeart Inc., Hsinchu (TW)

(72) Inventors: Bing-Jhang Wu, Chiayi (TW); Chih-Wei Liu, Taipei (TW); Po-Wei Huang, Yunlin County (TW); Bing-Fei Wu, Hsinchu (TW)

(73) Assignee: FACEHEART INC., Hsinchu (TW)

( * ) Notice: Subject to any disclaimer, the term of this patent is extended or adjusted under 35 U.S.C. 154(b) by 367 days.

(21) Appl. No.: 16/945,895

(22) Filed: Aug. 2, 2020

(65) Prior Publication Data

US 2021/0251567 A1 Aug. 19, 2021

(30) Foreign Application Priority Data

Feb. 19, 2020 (TW) ................. 10910532.2

(51) Int. Cl.
| | | |
|---|---|---|
| *A61B 5/00* | (2006.01) | |
| *A61B 5/0205* | (2006.01) | |
| *A61B 5/026* | (2006.01) | |
| *A61B 5/029* | (2006.01) | |
| *A61B 5/1455* | (2006.01) | |

(Continued)

(52) U.S. Cl.
CPC .............. *A61B 5/48* (2013.01); *A61B 5/0205* (2013.01); *A61B 5/02007* (2013.01); *A61B 5/029* (2013.01); *A61B 5/0261* (2013.01); *A61B 5/14551* (2013.01); *A61B 5/4368* (2013.01); *A61B 5/4393* (2013.01); *A61B 5/7278* (2013.01); *G06V 40/15* (2022.01);

(Continued)

(58) Field of Classification Search
CPC ..... A61B 5/48; A61B 5/02007; A61B 5/0205; A61B 5/0261; A61B 5/029; A61B 5/14551; A61B 5/4368; A61B 5/4393; A61B 5/7278; A61B 5/021; A61B 5/02416; A61B 5/0816; A61B 5/117; A61B 5/6897; A61B 5/6898; A61B 5/7239; A61B 5/728; G06V 40/45; G06V 40/15; G06V 40/166; G06K 9/00543

See application file for complete search history.

(56) References Cited

U.S. PATENT DOCUMENTS

2020/0342086 A1\* 10/2020 Oung .................. H04L 63/0861
2021/0150178 A1\* 5/2021 Wang ................. G06V 40/1347

FOREIGN PATENT DOCUMENTS

CN 105787420 A \* 7/2016 ............... A61B 5/01

\* cited by examiner

*Primary Examiner* — Edward F Urban
*Assistant Examiner* — Wassim Mahrouka

(57) ABSTRACT

A device for liveness detection is disclosed. The liveness detecting device has a simplest structure that principally comprises a light sensing unit and a signal processing module. Particularly, the signal processing module is configured for having a physiological feature extracting unit and a liveness detecting unit therein. The physiological feature extracting unit is adopted for extracting a first physiological feature from a PPG signal, or extracting a second physiological feature from the PPG signal that has been applied with a signal process. As such, through the first and second physiological features, the liveness detecting unit is able to determine whether a subject is a living body or not. The liveness detecting device does not use any camera unit and iPPG technology, such that the liveness detecting device has advantages of simple structure, low cost and immediately completing liveness detection.

19 Claims, 12 Drawing Sheets

(51) Int. Cl.
  *A61B 5/02* (2006.01)
  *G06V 40/10* (2022.01)
  *G06V 40/16* (2022.01)
  *A61B 5/08* (2006.01)
  *A61B 5/021* (2006.01)
  *A61B 5/024* (2006.01)

(52) U.S. Cl.
  CPC ............ *G06V 40/166* (2022.01); *A61B 5/021* (2013.01); *A61B 5/02416* (2013.01); *A61B 5/0816* (2013.01)

(a): PPG (b): VPG (c): APG

DEVICE AND METHOD FOR LIVENESS DETECTION

BACKGROUND OF THE INVENTION

1. Field of the Invention

The present invention relates to the technology field of liveness detection, and more particularly to a device and a method for liveness detection, wherein the device (method) is configured for completing a liveness detecting procedure without using any camera devices or image capturing units. Moreover, the device (method) can be applied in a physiological signal measurement system and/or an individual identification system.

2. Description of the Prior Art

Biometric identification makes use of unique human characteristics, including physiological characteristics and behavior characteristics. The physiological characteristics are well known including fingerprint, palm print, vein distribution pattern, pattern of iris, retina, facial features, and voice tone. On the other hand, personal handwriting style is known one kind of behavior characteristic. Currently, technologies of iris pattern recognition, fingerprint recognition, and face recognition have been widely applied in individual identification systems.

For example, when an individual identification system utilizes the face recognition technology to achieve an individual identification for a subject, a camera device is firstly controlled to capture at least one image frame of the subject. Therefore, after extracting a plurality of facial features from the image frame, comparison between a plurality of reference facial features that are stored in data based and the facial features is subsequently finished, so as to complete the individual identification of the subject. However, experience of practically using the face recognition-based individual identification system has revealed that, it is possible for person A to use person B's image so as to successfully cheat the individual identification system in a face recognition-based individual identification procedure. For example, person A can hold a picture, a video or a paper that contains person B's image to face an image capturing unit of the individual identification system, thereby making the individual identification system complete the individual identification procedure.

The forgoing person B's image contained in a picture, a video or a paper is called a fake image. Accordingly, there are various liveness detection technologies developed and then applied in the conventional individual identification system(s), so as to prevent the individual identification system from being cheated by the fake image in a face recognition-based individual identification procedure. China patent publication No. CN106845395A discloses a human face recognition method, comprising following steps:

(1) capturing a plurality of image frames from a subject, and then arranging the plurality of image frames in sequence based on a frame rate;
(2) detecting a face region of each of the image frames, and then produce a plurality of face ROIs;
(3) extracting green channel pixel values from each of the plurality of face ROIs, so as to obtain a green channel pixel signal after arranging the green channel pixel values that are extracted from each of the plurality of face ROIs in turns;
(4) applying a noise filtering process and a Fourier transform process to the green channel pixel signal, thereby producing a frequency signal of the pixel value sequence;
(5) achieving a heart rate calculation of the subject based on the frequency signal; and
(6) verifying the subject as a living body in case of the heart rate being determined to fall into a range between 45 bpm and 120 bpm.

Briefly speaking, China patent publication No. CN106845395A mainly utilizes an imaging photoplethysmography (iPPG) technology to obtain the green channel pixel signal from the face ROIs, so as to produce the frequency signal of the green channel pixel signal by applying a noise filtering process and a Fourier transform process to the green channel pixel signal. Consequently, after completing a heart rate calculation of the subject based on the frequency signal, it is able to verify whether the subject is a living body or not. Herein, the forgoing face ROI means a region of interest (ROI) that merely contains face image in each of the plurality of image frames. It is a pity that, the above-mentioned human face recognition method may still be cheated by a fake image of the subject. As described in more detail below, by producing a periodic variation of lights and shadows on the fake image or shaking the fake image have a periodically, the individual identification system can still complete a heart rate calculation on a frequency signal that is obtained after a noise filtering process and a Fourier transform process is applied to a green channel pixel signal. Therefore, it is understood that, by changing the periodic variation of lights and shadows and the shaking rate, the heart rate calculated by the individual identification system may fall into 45-120 bpm, thereby successfully cheating the individual identification system by using the fake image of the subject. On the other hand, it is worth noting that, the individual identification system must collect adequate image frames from the subject for making the heart rate calculation result be correct. From example, page 8 of specification of the China publication No. CN106845395A has suggested that a proper number of the image frames is 600.

On the other hand, Taiwan Patent No. 1539383 discloses a living body detection method for use in a face identification control system. The disclosed method comprises following steps:

(1a) capturing a plurality of image frames from a subject, and then detecting a face part in each of the image frames, thereby producing a plurality of face ROIs;
(2a) extracting red, green and blue channel pixel values from each of the plurality of face ROIs so as to obtain a red channel pixel signal, a green channel pixel signal and a blue channel pixel signal, and then producing a red channel frequency signal, a green channel frequency signal and a blue channel frequency signal by applying a Fourier transform process to the red channel pixel signal, the green channel pixel signal and the blue channel pixel signal;
(3a) obtaining a normalized random value by applying a normalized random value calculation to the red channel frequency signal, the green channel frequency signal and the blue channel frequency signal; and
(4a) in case of the random value according with a threshold value, the subject is verified as a living body.

It is a pity that, the conventional living body detection method may still be cheated by a fake image of the subject. As described in more detail below, by producing a periodic variation of lights and shadows on the fake image or shaking the fake image have a periodically, the living body detection method can still complete the calculation of the normalized random value. Therefore, it is understood that, by changing the periodic variation of lights and shadows and the shaking rate, the normalized random value may accord with the threshold value.

From above descriptions, it is understood that the conventionally-used living body detecting methods still have room for improvement. In view of that, inventors of the present application have made great efforts to make inventive research and eventually provided a device and a method for liveness detections.

SUMMARY OF THE INVENTION

The primary objective of the present invention is to disclose a device and a method for liveness detection, wherein the liveness detecting device can be an independent electronic device, or be integrated in an individual identification system or a physiological signal measurement system. The liveness detecting device has a simplest structure that merely comprises a light sensing unit and a signal processing module. Particularly, the signal processing module is configured for having a physiological feature extracting unit and a liveness detecting unit therein. The physiological feature extracting unit is adopted for extracting a first physiological feature from a PPG signal, or extracting a second physiological feature from the PPG signal that has been applied with a signal process. As such, through the first and second physiological features, the liveness detecting unit is able to determine whether a subject is a living body or not. The liveness detecting device does not use any camera unit and iPPG technology, such that the liveness detecting device has advantages of simple structure, low cost and immediately completing liveness detection.

In order to achieve the forgoing primary objective, the present invention provides an embodiment of the device for liveness detection, comprising:
a light sensing unit, being used for facing a sensing portion of a subject, so as to collect a diffuse light from the sensing portion; and
a signal processing module, comprising:
  a signal processing unit;
  a control unit, being coupled to the signal processing unit and the light sensing unit, so as to control the light sensing unit to collect the diffuse light from the sensing portion;
  a signal receiving unit, being coupled to the light sensing unit and the signal processing unit, so as to receive the diffuse light from the light sensing unit and subsequently transmit a physiological signal to the signal processing unit, such that the signal processing unit obtains at least one physiological data by applying at least one signal process to the physiological signal;
  a physiological feature extracting unit, being coupled to the signal receiving unit, and being configured for extracting a first physiological feature from the physiological signal, or extracting a second physiological feature from the physiological signal that has been applied with at least one signal process; and
  a liveness detecting unit, being coupled the signal processing unit and the physiological feature extracting unit;
wherein the liveness detecting unit is configured for determining whether the subject is a living body or not according to the first physiological features and/or second physiological features;
wherein the liveness detecting unit is also able to determine whether the subject is a living body or not based on the physiological data received from the signal processing unit.

Moreover, the present invention also provides an embodiment of the method for liveness detection, comprises:
(1) using a light sensing unit to collect a diffuse light that is radiated from a sensing portion of a subject;
(2) letting a signal receiving unit receive the diffuse light transmitted from the light sensing unit, and subsequently transmit a physiological signal to a signal processing unit;
(3) configuring a physiological feature extracting unit to extract a first physiological feature from the physiological signal, or to extract a second physiological feature from the physiological signal that has been applied with at least one signal process; and
(4) providing a liveness detecting unit coupled to the signal processing unit and the physiological feature extracting unit, wherein the liveness detecting unit is configured for determining whether the subject is a living body or not according to the first physiological features and/or second physiological features; wherein the liveness detecting unit is also able to determine whether the subject is a living body or not based on the physiological data that is produced after the signal processing unit completes at least one signal process of the physiological signal.

In one embodiment, the forgoing device and method can be applied in an electronic system that is selected from the group consisting of individual identification system and physiological signal measurement system. In which, the forgoing individual identification system is selected from the group consisting of laptop computer integrated with functionality of individual identification, tablet PC integrated with functionality of individual identification, smartphone integrated with functionality of individual identification, electric door lock integrated with functionality of individual identification, entrance intercom system with functionality of individual identification, and automated teller machine (ATM) with functionality of individual identification. Moreover, the forgoing physiological signal measurement system comprises an electronic host device that is selected from the group consisting of all-in-one personal computer, desk computer, laptop computer, tablet PC, smartphone, smart watch, smart wristband, infrared thermometer, and pulse oximeter.

In one embodiment, the physiological data comprises at least one physiological index that is selected from the group consisting of blood volume, heart rate, respiratory rate, arterial oxygen saturation, blood pressure, blood vessel viscosity, venous function, venous reflux, ankle pressure, genital response, and cardiac output.

In one embodiment, the physiological signal is a photoplethysmography (PPG) signal, and the first physiological features are selected from the group consisting of a plurality of waveform features in the PPG signal, at least one waveform feature for describing arterial oxygen extracted from the PPG signal, at least one waveform feature for describing blood pressure extracted from the PPG signal, and at least one waveform feature for describing respiratory extracted from the PPG signal.

In one embodiment, the physiological signal that has been applied with the signal process is selected from the group consisting of first derivative PPG signal, second derivative PPG signal, third derivative PPG signal, and fourth derivative PPG signal.

In one embodiment, the second physiological features are extracted from the first derivative PPG signal, and being selected from the group consisting of a plurality of waveform features in the first derivative PPG signal, at least one waveform feature for describing arterial oxygen extracted from the first derivative PPG signal, at least one waveform feature for describing blood pressure extracted from the first derivative PPG signal, and at least one waveform feature for describing respiratory extracted from the first derivative PPG signal.

In one embodiment, the second physiological features are extracted from the second derivative PPG signal, and being selected from the group consisting of a plurality of waveform features in the second derivative PPG signal, at least one waveform feature for describing arterial oxygen extracted from the second derivative PPG signal, at least one waveform feature for describing blood pressure extracted from the second derivative PPG signal, and at least one waveform feature for describing respiratory extracted from the second derivative PPG signal.

In one embodiment, the second physiological features are extracted from the third derivative PPG signal, and being selected from the group consisting of a plurality of waveform features in the third derivative PPG signal, at least one waveform feature for describing arterial oxygen extracted from the third derivative PPG signal, at least one waveform feature for describing blood pressure extracted from the third derivative PPG signal, and at least one waveform feature for describing respiratory extracted from the third derivative PPG signal.

In one embodiment, the second physiological features are extracted from the fourth derivative PPG signal, and being selected from the group consisting of a plurality of waveform features in the fourth derivative PPG signal, at least one waveform feature for describing arterial oxygen extracted from the fourth derivative PPG signal, at least one waveform feature for describing blood pressure extracted from the fourth derivative PPG signal, and at least one waveform feature for describing respiratory extracted from the fourth derivative PPG signal.

In one embodiment, the plurality of waveform features in the PPG signal comprise: time interval of systolic wave, time interval of dicrotic wave, time interval of diastolic wave, existence of systolic notch in the forgoing systolic wave, existence of systolic peak in the forgoing systolic wave, existence of dicrotic notch in the forgoing dicrotic wave, existence of diastolic peak in the forgoing diastolic wave, waveform area of the forgoing systolic wave, waveform area of the forgoing dicrotic wave, waveform area of the forgoing diastolic wave, peak value of the forgoing systolic peak, peak value of the forgoing diastolic peak, slope of the forgoing dicrotic notch, time interval between two of the forgoing systolic notches, time interval between two of the forgoing systolic peaks, time interval between two of the forgoing dicrotic notches, time interval between two of the forgoing diastolic peaks, waveform area relativity between the forgoing diastolic wave and the forgoing dicrotic wave, peak value relativity between the forgoing systolic peak and the forgoing dicrotic notch, peak value relativity between the forgoing diastolic peak and the forgoing dicrotic notch.

In one embodiment, the plurality of waveform features in the PPG signal comprise: a first peak point, a first zero-crossing point, a first valley point, a second zero-crossing point, a second peak point, a second valley point, time interval between any two of the forgoing points, value relativity between any two of the forgoing points.

In one embodiment, the plurality of waveform features in the PPG signal comprise: early systolic positive wave, early systolic negative wave, late systolic re-increasing wave, late systolic re-decreasing wave, early diastolic positive wave, time interval between any two of the forgoing waves, and peak value relativity between any two of the forgoing waves.

In one embodiment, the device for liveness detection further comprises a data outputting unit, which is coupled to the signal processing unit for facilitating the signal processing unit output the physiological data.

In one embodiment, the device for liveness detection further comprises a sensing portion labeling unit, which is controlled by the control unit for producing a mark on the sensing portion of the subject. Wherein the sensing portion is a body surface or a non-body surface of the subject, and the mark is selected from the group consisting of light spot, pattern, symbol, and text.

In one embodiment, the device for liveness detection further comprising:
a lighting unit; and
a driving unit, being provided in the signal processing module, and being coupled to control unit and the lighting unit;
wherein the driving unit is controlled by the control unit, so as to drive the lighting unit project a detecting light to the sensing portion of the subject, thereby making the diffuse light be radiated from the sensing portion.

In one embodiment of the method for liveness detection, before the step (1) is executed, a lighting unit being controlled to project a detecting light to the sensing portion of the subject, and a sensing portion labeling unit is subsequently controlled to produce a mark on the sensing portion of the subject.

In one embodiment of the method for liveness detection, after completing the step (2) and before executing the step (3), a physiological feature enhancing unit is provided to be coupled between the signal receiving unit and the physiological feature extracting unit, thereby applying a physiological feature enhancing process to the physiological signal.

BRIEF DESCRIPTION OF THE DRAWINGS

The invention as well as a preferred mode of use and advantages thereof will be best understood by referring to the following detailed description of an illustrative embodiment in conjunction with the accompanying drawings, wherein.

DETAILED DESCRIPTION OF THE PREFERRED EMBODIMENTS

To more clearly describe a device and method for liveness detection disclosed by the present invention, embodiments of the present invention will be described in detail with reference to the attached drawings hereinafter.

First Embodiment

Figure 1:
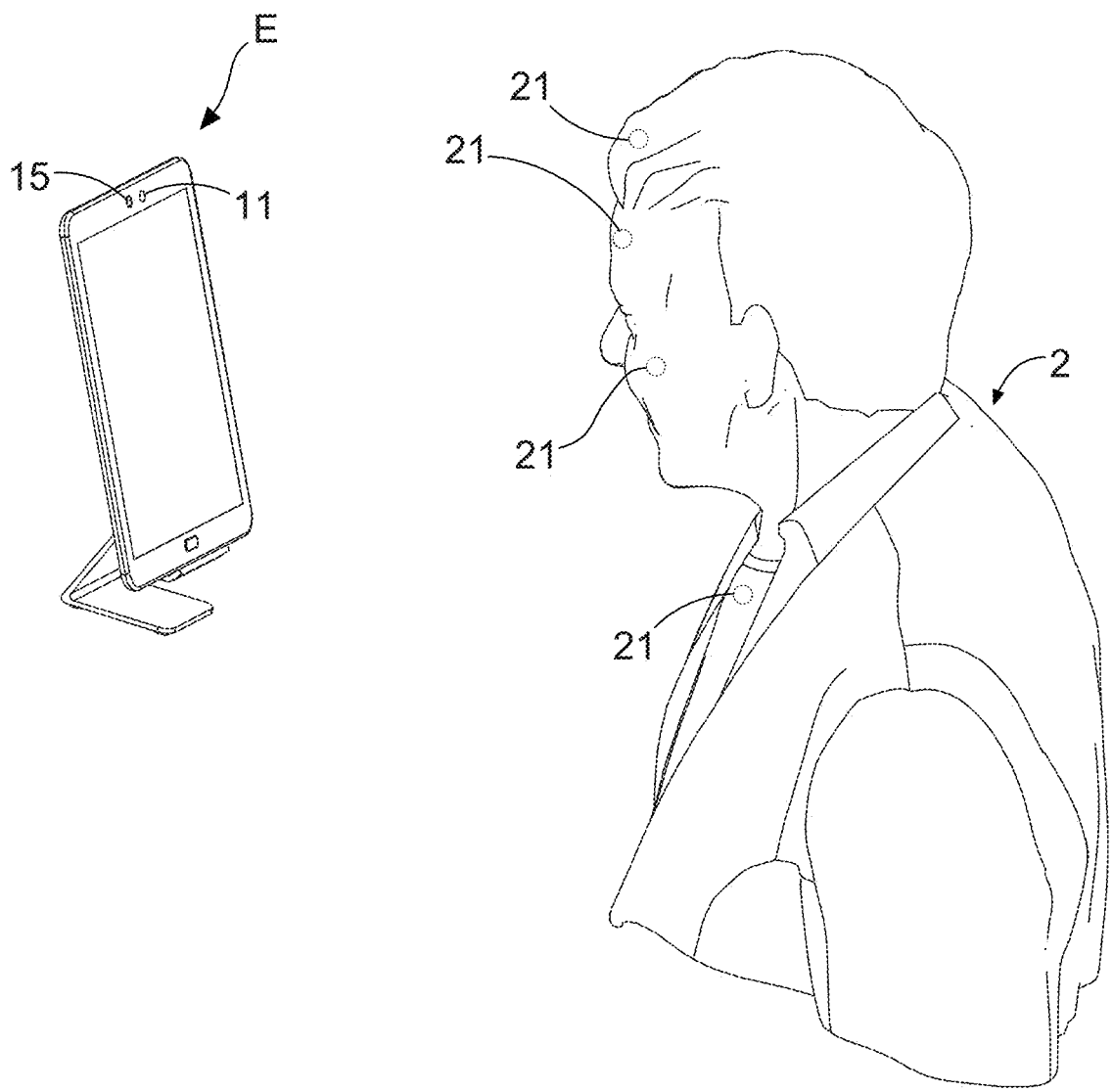
FIG. 1 shows a stereo diagram of an individual identification system that is integrated with a device for liveness detection according to the present invention.
Figure 2:
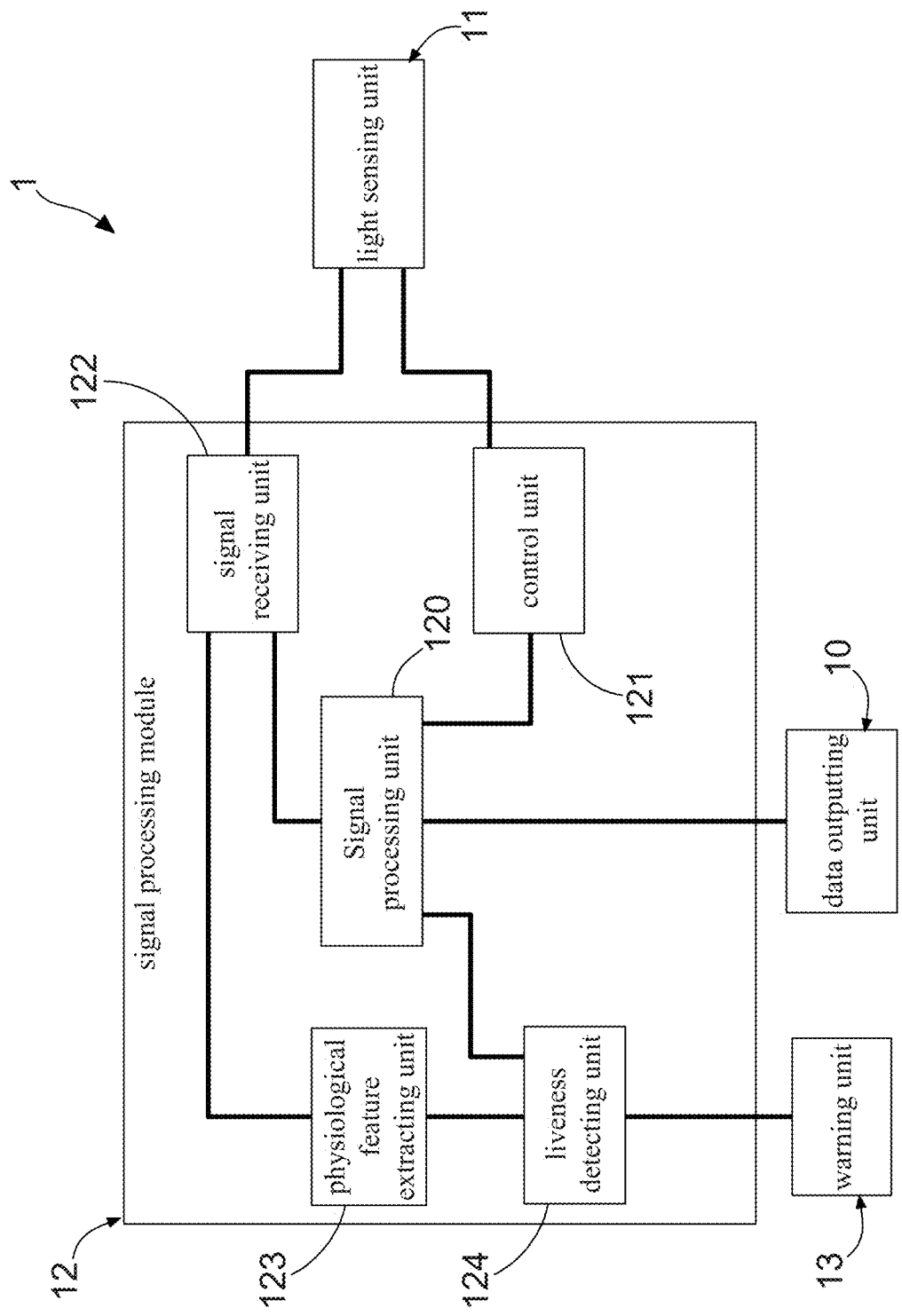
FIG. 2 shows a block diagram of a first embodiment of the device for liveness detection according to the present invention.
Figure 3A:
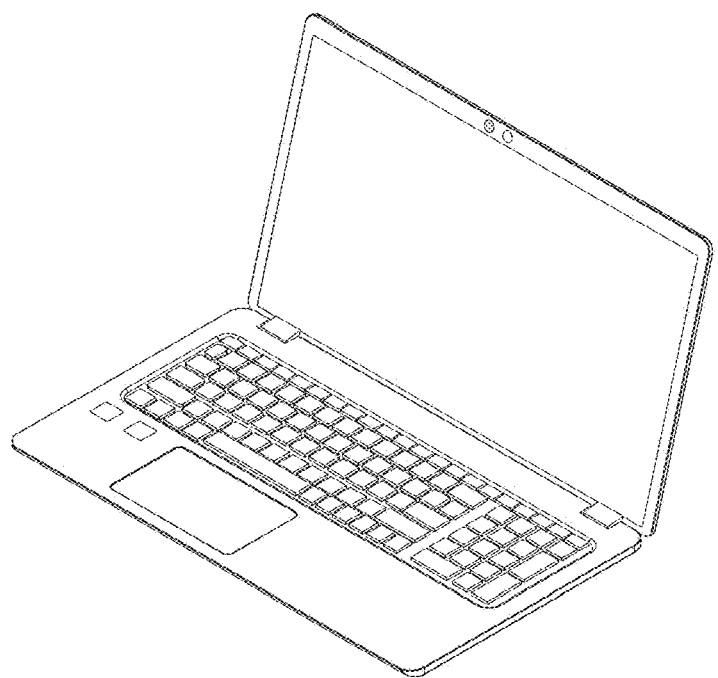
FIG. 3A shows a stereo diagram of a laptop computer integrated with functionality of individual identification.
Figure 3B:
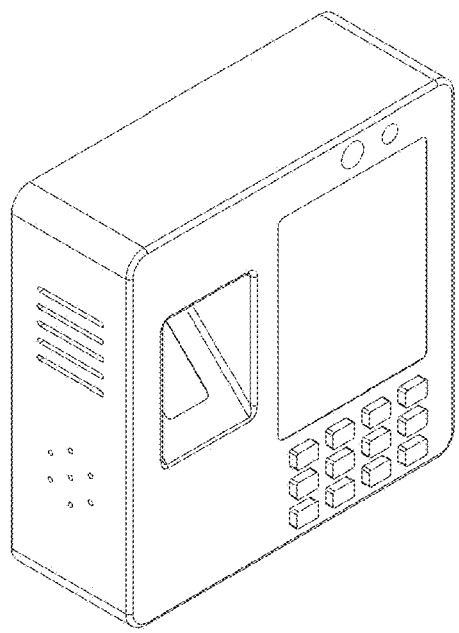
FIG. 3B shows a stereo diagram of an entrance intercom system integrated with functionality of individual identification.
Figure 3C:
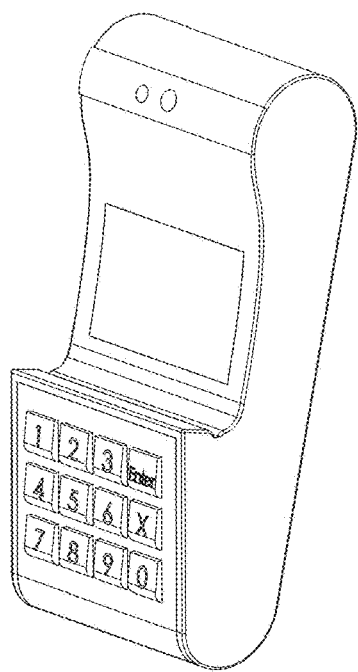
FIG. 3C shows a stereo diagram of an electric door lock integrated with functionality of individual identification.
Figure 3D:
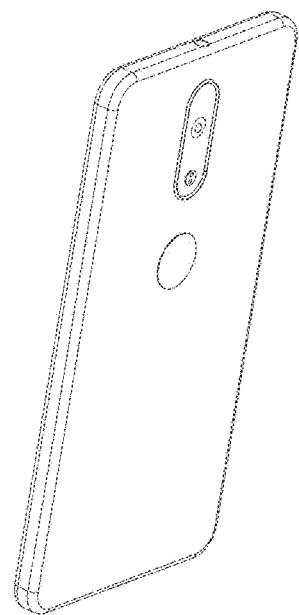
FIG. 3D shows a stereo diagram of a smartphone integrated with functionality of individual identification.
Figure 3E:
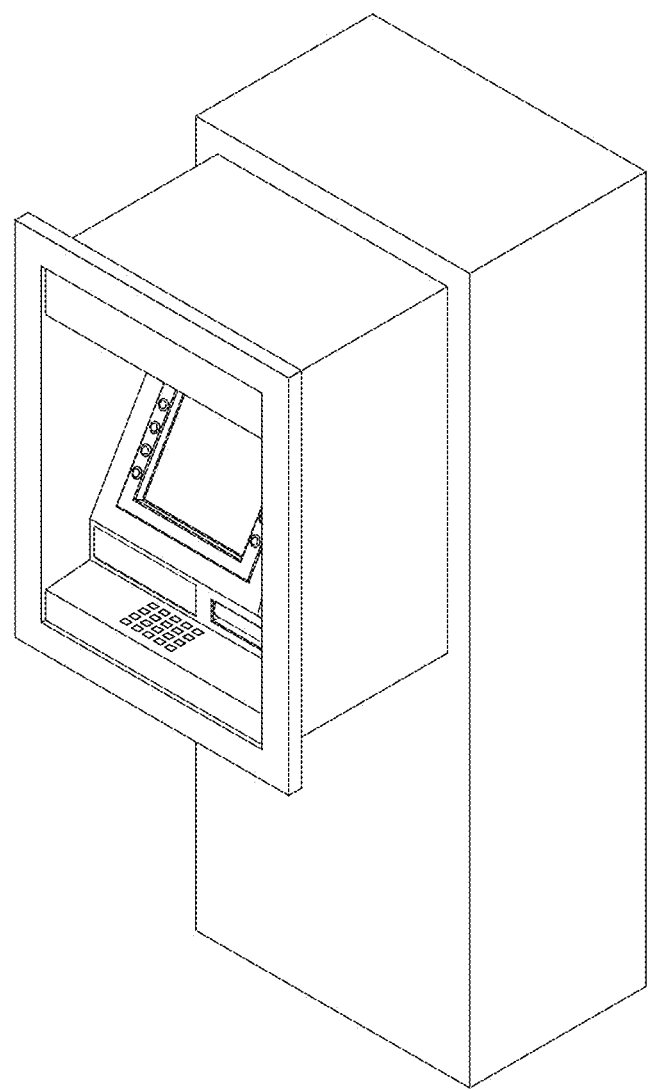
FIG. 3E shows a stereo diagram of an automated teller machine (ATM) integrated with functionality of individual identification.

With reference to FIG. 1, there is shown a stereo diagram of an individual identification system that is integrated with a device for liveness detection according to the present invention. Moreover, FIG. 2 illustrates a block diagram of a first embodiment of the device for liveness detection according to the present invention. The liveness detecting device 1 of the present invention can be an independent electronic device, or be integrated in an individual identification system E (as FIG. 1) or a physiological signal measurement system. It is worth explaining that, the individual identification system E integrated with the liveness detecting device 1 of the present invention fails to be cheated by a fake image of a subject in a face recognition-based individual identification procedure. Although FIG. 1 depicts that a tablet PC is adopted for being an electronic host deice of the individual identification system E, the tablet PC is not used as a limitation for the practicable embodiment of the electronic host device. It should know that, there are various commercial electronic device integrated with functionality of individual identification. For example, FIG. 3A shows a laptop computer integrated with functionality of individual identification, FIG. 3B shows an entrance intercom system integrated with functionality of individual identification, FIG. 3C shows an electric door lock integrated with functionality of individual identification, FIG. 3D shows smartphone integrated with functionality of individual identification, and FIG. 3E shows an automated teller machine (ATM) integrated with functionality of individual identification.

Figure 4A:
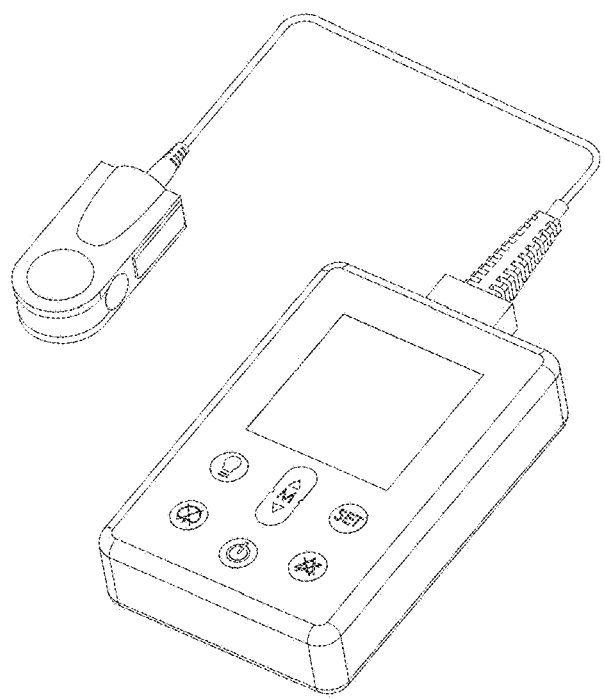
FIG. 4A shows a stereo diagram of a pulse oximeter integrated with the device for liveness detection according to the present invention.
Figure 4B:
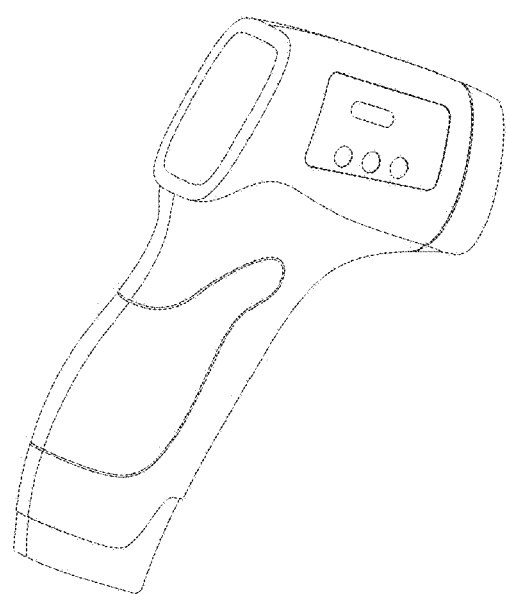
FIG. 4B shows a stereo diagram of an infrared thermometer integrated with the device for liveness detection according to the present invention.

In addition, the liveness detecting device 1 of the present invention can also be integrated in a physiological signal measurement system. For instance, FIG. 4A shows a pulse oximeter integrated with the liveness detecting device 1 of the present invention, and FIG. 4B shows an infrared thermometer integrated with the liveness detecting device 1 of the present invention. Of course, the physiological signal measurement system certainly comprises an electronic host device for utilizing imaging photoplethysmography (iPPG) technology and/or remote photoplethysmography (rPPG) technology to achieve a physiological signal measurement. In a practicable embodiment, the forgoing electronic host device can be an all-in-one personal computer, a desk computer, a laptop computer, a tablet PC, a smartphone, a smart watch, a smart wristband, an infrared thermometer, or a pulse oximeter.

Please refer to FIG. 1 and FIG. 2 again. In first embodiment, the liveness detecting device 1 mainly comprises a light sensing unit 11 and a signal processing module 12. As described in more detail below, the light sensing unit 11 is used for facing a sensing portion 21 of a subject 2, so as to collect a diffuse light from the sensing portion 21. It is worth explaining that, the diffuse light is a single-wavelength light or a multi-wavelength light that is radiated from the sensing portion 21 in case of the subject 2 is exposed under an ambient light. In the present invention, the ambient light can be a natural light and an artificial light. Therefore, relying on the type of the diffuse light, it is understood that the light sensing unit 11 can be a single point photo sensor, a matrix photo sensor, a one-channel image sensor, or a multi-channel image sensor As described in more detail below, the signal processing module 12 comprises a signal processing unit 120, a control unit 121, a signal receiving unit 122, a physiological feature extracting unit 123, and a liveness detecting unit 124. The control unit 121 is coupled to the signal processing unit 120 and the light sensing unit 11, so as to control the light sensing unit 11 to collect the diffuse light from the sensing portion 21. On the other hand, the signal receiving unit 122 is coupled to the light sensing unit 11 and the signal processing unit 120, so as to receive the diffuse light from the light sensing unit 11, and subsequently transmit a physiological signal to the signal processing unit 120. As such, the signal processing unit 120 is able to obtain at least one physiological data by applying at least one signal process to the physiological signal. In a general case, the physiological data comprises at least one physiological index that is selected from the group consisting of blood volume, heart rate, respiratory rate, arterial oxygen saturation, blood pressure, blood vessel viscosity, venous function, venous reflux, ankle pressure, genital response, and cardiac output.

FIG. 1 also depicts that the liveness detecting device 1 of the present invention further comprises a data outputting unit 10, which is coupled to the signal processing unit 120 for facilitating the signal processing unit 120 output the physiological data. In a practicable embodiment, the data outputting unit 10 can be a display unit, a loudspeaker, a wired transmission interface, or a wireless transmission interface.

Figure 5:
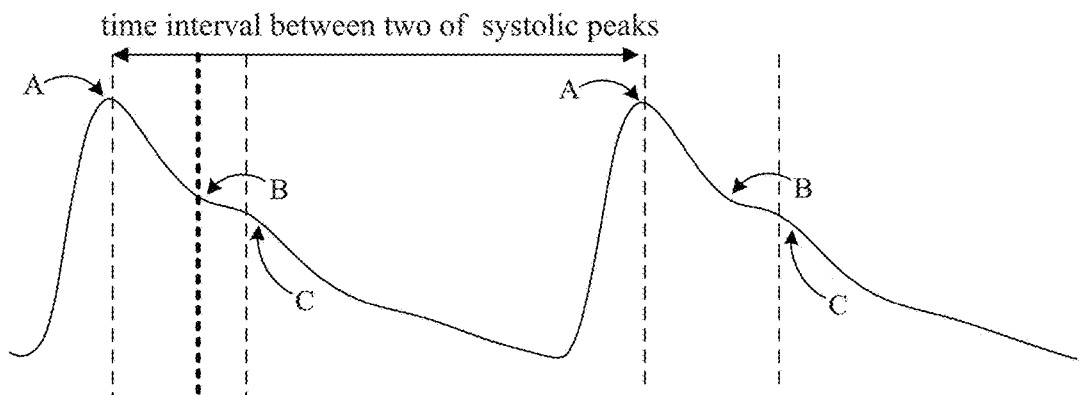
FIG. 5 shows a waveform diagram that depicts a photoplethysmography (PPG) signal, a velocity photoplethysmography (VPG) signal, and an acceleration photoplethysmography (APG) signal.
Figure 5:
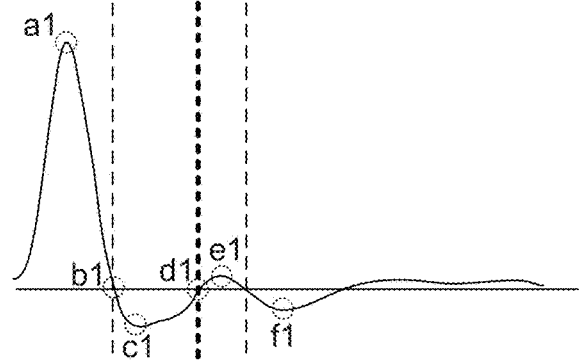
Figure 5:
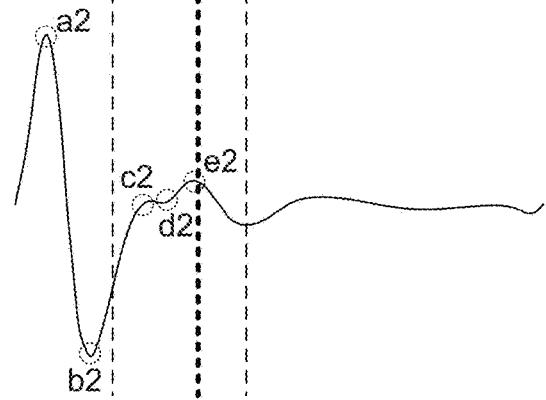

In the signal processing module 12, the physiological feature extracting unit 123 is coupled to the signal receiving unit 122, and is configured for extracting a first physiological feature from the physiological signal. It is worth explaining that, the aforesaid physiological signal is a photoplethysmography (PPG) signal, and the forgoing first physiological features are selected from the group consisting of a plurality of waveform features in the PPG signal, at least one waveform feature for describing arterial oxygen extracted from the PPG signal, at least one waveform feature for describing blood pressure extracted from the PPG signal, and at least one waveform feature for describing respiratory extracted from the PPG signal. FIG. 5 shows a waveform diagram that depicts a photoplethysmography (PPG) signal, a velocity photoplethysmography (VPG) signal, and an acceleration photoplethysmography (APG) signal. In FIG. 5, the PPG signal contains two systolic waves, two dicrotic waves and diastolic waves, wherein points A, B and C represent a systolic peak in the systolic wave, a dicrotic notch in the dicrotic wave and diastolic peak in the diastolic wave, respectively.

In the present invention, the aforesaid waveform features in the PPG signal comprise: time interval of systolic wave, time interval of dicrotic wave, time interval of diastolic wave, existence of systolic notch in the systolic wave, existence of systolic peak in the systolic wave, existence of dicrotic notch in the dicrotic wave, existence of diastolic peak in the diastolic wave, waveform area of the systolic wave, waveform area of the dicrotic wave, waveform area of the diastolic wave, peak value of the systolic peak, peak value of the diastolic peak, slope of the dicrotic notch, time interval between two of the systolic notches, time interval between two of the systolic peaks, time interval between two of the dicrotic notches, time interval between two of the diastolic peaks, waveform area relativity between the diastolic wave and the dicrotic wave, peak value relativity between the systolic peak and the dicrotic notch, peak value relativity between the diastolic peak and the dicrotic notch.

On the other hand, the physiological feature extracting unit 123 can also extract a second physiological feature from the physiological signal that has been applied with at least one signal process, wherein the afore said physiological signal that has been applied with the signal process may be a first derivative PPG signal, a second derivative PPG signal, a third derivative PPG signal, or a fourth derivative PPG signal according to the signal process. For example, FIG. 5 shows the first derivative PPG signal is regarded as a velocity photoplethysmography (VPG) signal, and the aforesaid second physiological features are extracted from the VPG signal, and are selected from the group consisting of a plurality of waveform features in the VPG signal, at least one waveform feature for describing arterial oxygen extracted from the VPG signal, at least one waveform feature for describing blood pressure extracted from the VPG signal, and at least one waveform feature for describing respiratory extracted from the VPG signal. It is worth noting that, the VPG signal in the FIG. 5 contains six feature points of a1, b1, c1, d1, e1, and f1, which are represent a first peak point, a first zero-crossing point, a first valley point, a second zero-crossing point, a second peak point, and a second valley point in the VPG signal, respectively.

Briefly speaking, after applying a first order differential process to the PPG signal, the physiological feature extracting unit 123 is able to extract several second physiological features from the VPG signal, including: first peak point (a1), first zero-crossing point (b1), first valley point (c1), second zero-crossing point (d1), second peak point (e1), second valley point (f1), time interval between any two of the forgoing points, and value relativity between any two of the forgoing points.

On the other hand, after applying a second order differential process to the PPG signal, the physiological feature extracting unit 123 is able to extract several second physiological features from the APG signal. For example, FIG. 5 shows the second derivative PPG signal (i.e., the APG signal) contains a plurality of features of early systolic positive wave, early systolic negative wave, late systolic re-increasing wave, late systolic re-decreasing wave, early diastolic positive wave, time interval between any two of the forgoing waves, and peak value relativity between any two of the forgoing waves. As described in more detail below, the early systolic positive wave, the early systolic negative wave, the late systolic re-increasing wave, the late systolic re-decreasing wave, and the early diastolic positive wave contains feature points of a2, b2, c2, d2, and e2, respectively.

Briefly speaking, after applying a second order differential process to the PPG signal, the physiological feature extracting unit 123 is able to extract several second physiological features from the APG signal, including: early systolic positive wave, early systolic negative wave, late systolic re-increasing wave, late systolic re-decreasing wave, early diastolic positive wave, time interval between any two of the forgoing waves, and peak value relativity between any two of the forgoing waves.

Please refer to FIG. 1 and FIG. 2 again. The liveness detecting unit 124 is coupled the signal processing unit 120 and the physiological feature extracting unit 123. In the present invention, the liveness detecting unit 124 is configured for determining whether the subject 2 is a living body or not according to the first physiological features and/or second physiological features. Moreover, the liveness detecting unit 124 is also able to determine whether the subject 2 is a living body or not based on the physiological data received from the signal processing unit 120. In addition, the physiological feature extracting unit 123 is able to further applying a third order differential process to the PPG signal, so as to extract several second physiological features from a third derivative PPG signal. Furthermore, it is possible for the physiological feature extracting unit 123 is able to further applying a fourth order differential process to the PPG signal, so as to extract several second physiological features from a fourth derivative PPG signal.

According to the particular design of the present invention, the liveness detecting unit 124 is also able to determine whether the subject 2 is a living body or not based on the physiological data received from the signal processing unit 120, wherein the physiological data comprises at least one physiological index that is selected from the group consisting of blood volume, heart rate, respiratory rate, arterial oxygen saturation, blood pressure, blood vessel viscosity, venous function, venous reflux, ankle pressure, genital response, and cardiac output. Herein, it is worth explaining that, the physiological feature extracting unit 123 and the liveness detecting unit 124 can be provided in the signal processing module 12 by a form of firmware, function library, application program, or operands.

During the operation of the liveness detecting device 1, the liveness detecting unit 124 would immediately verify the subject 2 as a living body in case of the sensing unit 11 collecting a diffuse light from a body surface of the subject as well as the physiological feature extracting unit 123 finding that the PPG signal contains features of normal living body. For example, FIG. 1 depicts that the body surface is a face cheek or a forehead of the subject 2. On the contrary, when the sensing unit 11 collecting a diffuse light from a non-body surface of the subject 2, such as hair or cloth, the liveness detecting unit 124 would not regard the subject 2 as a living body even if the physiological feature extracting unit 123 finds that the PPG signal contains features of normal living body. In such case, a warning unit 13 coupled to the liveness detecting unit 124 is activated to generate a warning signal, wherein the warning signal is selected from the group consisting of light signal, sound signal, acousto-optic signal, text signal, symbol signal, pattern signal, and image signal.

Second Embodiment

Figure 6:
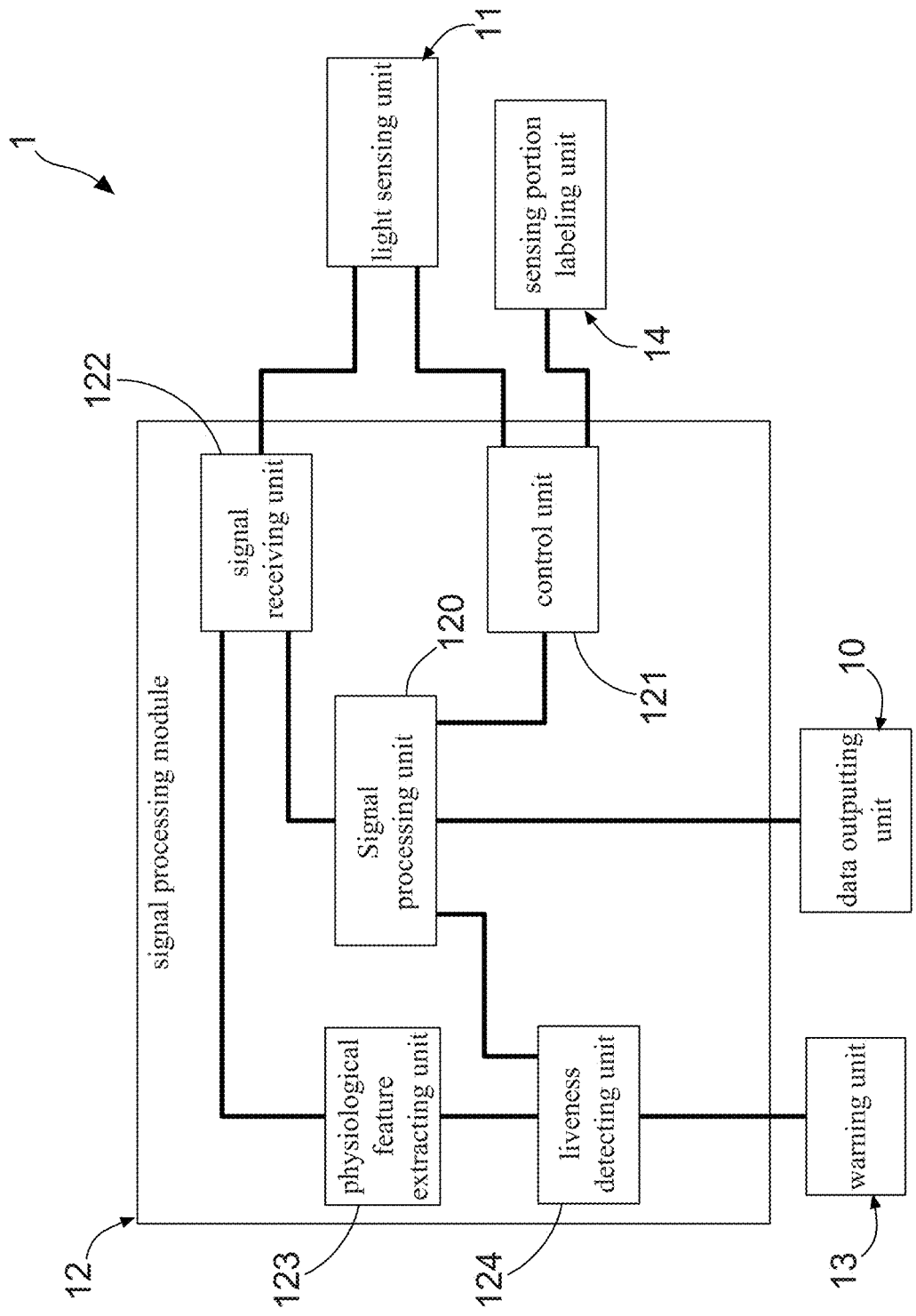
FIG. 6 shows a block diagram of a second embodiment of the device for liveness detection according to the present invention.

Referring to FIG. 1 again, and please simultaneously refer to FIG. 6, which shows a block diagram of a second embodiment of the device for liveness detection according to the present invention. After comparing FIG. 6 with FIG. 2, it is understood that second embodiment of the liveness detecting device 1 of the present invention further comprises a sensing portion labeling unit 14. As FIG. 6 shows, the sensing portion labeling unit 14 is coupled to and controlled by the control unit 121, so as to produce a mark on the sensing portion 21 of the subject 2. As such, a user of the liveness detecting device 1 is facilitated to know that the sensing portion 21 labeled with the mark is a body surface or a non-body surface. In a practicable embodiment, the mark can be a light spot, a pattern, a symbol, or a text. Briefly speaking, before executing a liveness detection procedure, the user can make the sensing portion labeling unit 14 of the liveness detecting device 1 project a mark onto a specific portion of the subject 2, so as to make sure the specific portion is a body surface of the subject 2. Consequently, the user can operate the liveness detecting device 1 to complete a liveness detection procedure of the subject 2 with high detection accuracy.

Third Embodiment

Figure 7:
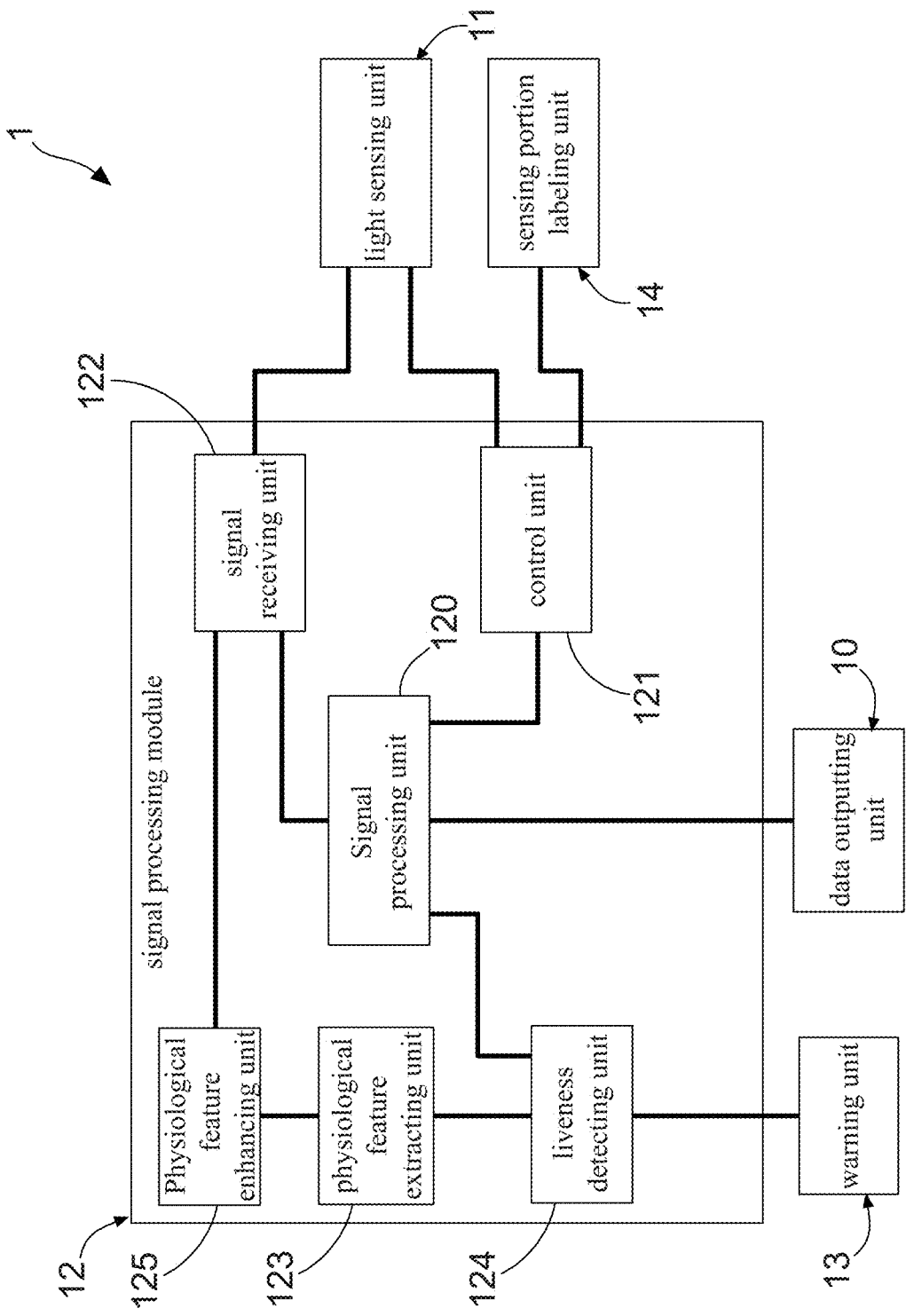
FIG. 7 shows a block diagram of a third embodiment of the device for liveness detection according to the present invention.

Referring to FIG. 1 again, and please simultaneously refer to FIG. 7, which shows a block diagram of a third embodiment of the device for liveness detection according to the present invention. After comparing FIG. 7 with FIG. 6, it is understood that third embodiment of the liveness detecting device 1 of the present invention further comprises a physiological feature enhancing unit 125. As FIG. 7 shows, the physiological feature enhancing unit 125 is provided in the signal processing module 12, and is coupled between the signal receiving unit 122 and the physiological feature extracting unit 123. In the present invention, the physiological feature enhancing unit 125 is used for applying a physiological feature enhancing process to the physiological signal before the physiological feature extracting unit 123 receives the physiological signal from the signal receiving unit 122. After being applied with the physiological feature enhancing, the first physiological features such as systolic peak (point A in FIG. 5), dicrotic notch (point B in FIG. 5) and diastolic peak (point C in FIG. 5) contained in the PPG signal would therefore highlighted. Of course, the physiological feature extracting unit 123 can be also configured for making other physiological features contained in the PPG signal be enhanced and highlighted, including: time interval between two of the systolic notches, time interval between two of the systolic peaks, time interval between two of the dicrotic notches, time interval between two of the diastolic peaks, waveform area relativity between the diastolic wave and the dicrotic wave, peak value relativity between the systolic peak and the dicrotic notch, peak value relativity between the diastolic peak and the dicrotic notch.

Fourth Embodiment

Figure 8:
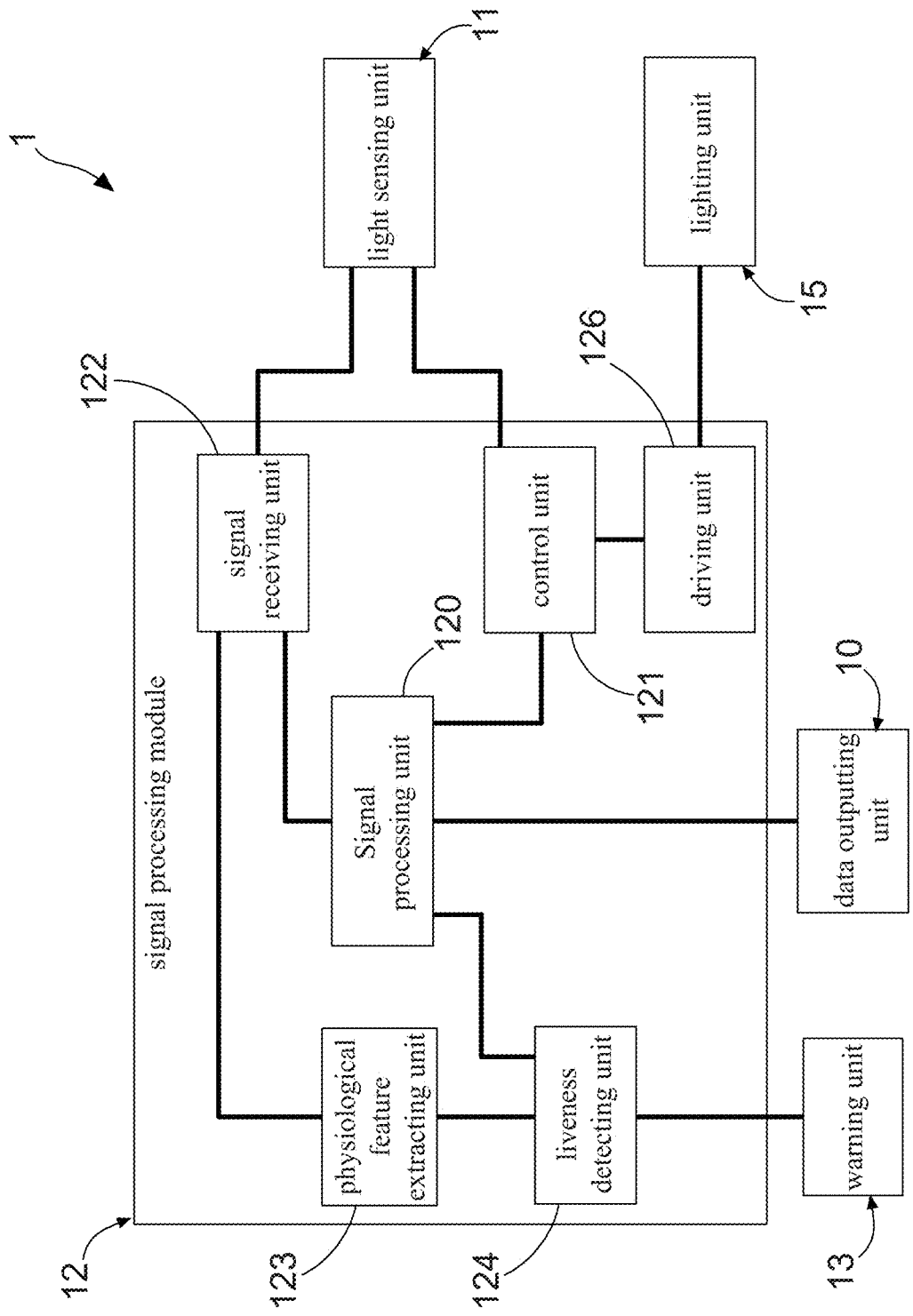
FIG. 8 shows a block diagram of a fourth embodiment of the device for liveness detection according to the present invention.

Referring to FIG. 1 again, and please simultaneously refer to FIG. 8, which shows a block diagram of a fourth embodiment of the device for liveness detection according to the present invention. After comparing FIG. 8 with FIG. 2, it is understood that fourth embodiment of the liveness detecting device 1 of the present invention further comprises a lighting unit 15 and a driving unit 126. As FIG. 8 shows, the driving unit 126 is provided in the signal processing module 12, and is coupled to control unit 121 and the lighting unit 15. In the present invention, the driving unit 126 is controlled by the control unit 121, so as to drive the lighting unit 15 project a detecting light to the sensing portion 21 of the subject 2, thereby making the diffuse light be radiated from the sensing portion 21. The detecting light is an artificial light, and the artificial light is a single-wavelength light or a multi-wavelength light. As described in more detail below, the lighting unit 15 comprises at least one lighting component that is selected from the group consisting of light-emitting diode (LED), vertical cavity surface emitting laser (VCSEL), and organic light-emitting diode (OLED). It is understood that, the forgoing LED can be a monochrome LED or an LED that is able to emit a poly-chromatic light comprising a green light (400-600 nm), red light (600-800 nm) and infrared light (800-1000 nm). Similarly, the OLED can also be a monochrome OLED or a poly-chromatic OLED.

Fifth Embodiment

Figure 9:
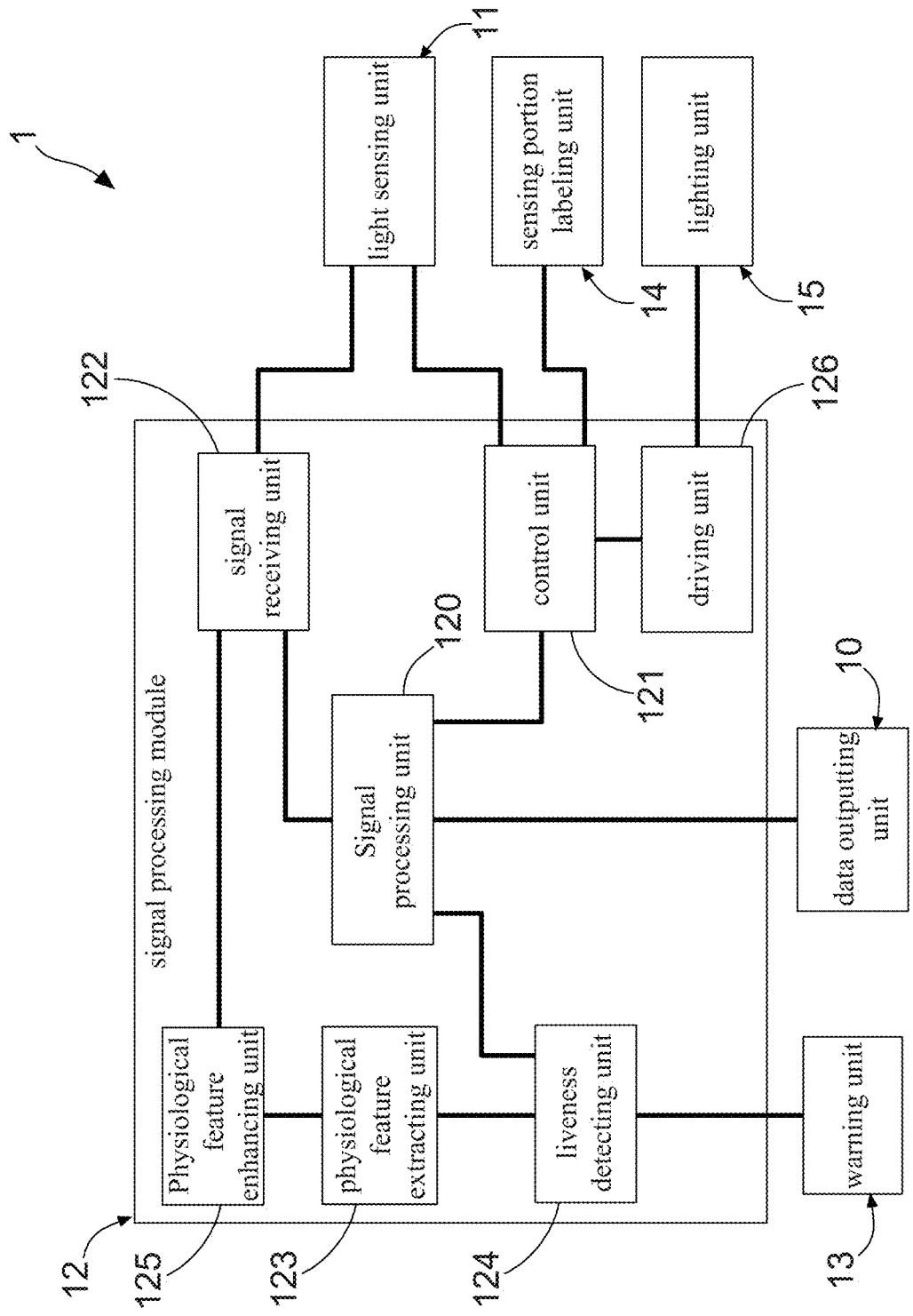
FIG. 9 shows a block diagram of a fifth embodiment of the device for liveness detection according to the present invention.

FIG. 9 illustrates a block diagram of a fifth embodiment of the device for liveness detection according to the present invention. After comparing FIG. 9 with FIG. 8, it is understood that fifth embodiment of the liveness detecting device 1 is obtained by adding the aforesaid physiological feature enhancing unit 125 and sensing portion labeling unit 14 into the framework of the forth embodiment.

Method for Liveness Detection

Figure 10:
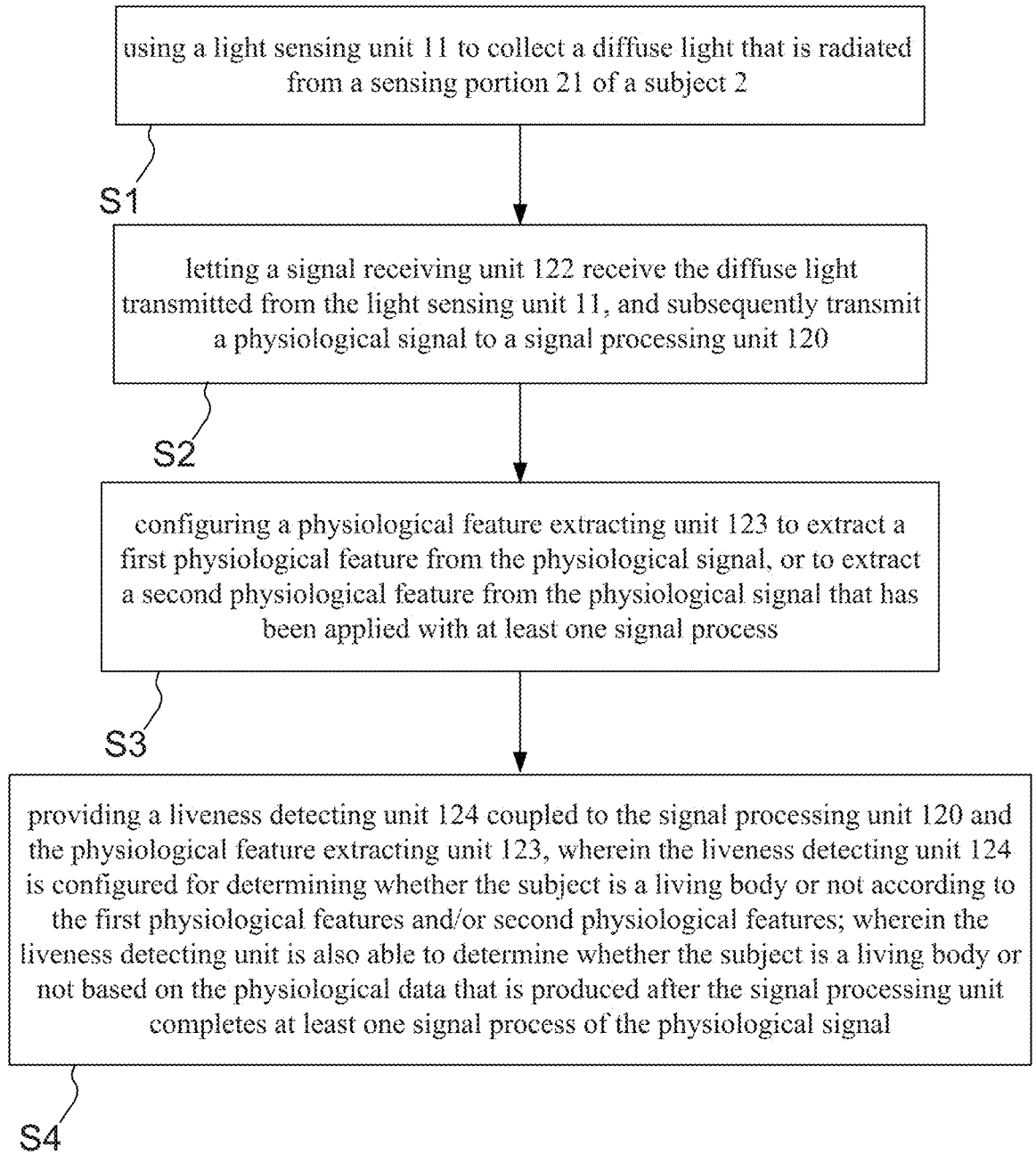
FIG. 10 shows a flowchart diagram of a method for liveness detection according to the present invention.

Referring to FIG. 1 and FIG. 2 again, and please simultaneously refer to FIG. 10, which illustrates a flowchart diagram of a method for liveness detection according to the present invention. As FIG. 1, FIG. 2 and FIG. 10 shows, flow of the method for liveness detection is firstly proceeded to step S1, so as to use a light sensing unit 11 to collect a diffuse light that is radiated from a sensing portion 21 of a subject 2. However, FIG. 6 particularly depicts that the liveness detecting device 1 of the present invention can further comprise a sensing portion labeling unit 14. Accordingly, before the step S1 is executed, it is able to control the sensing portion labeling unit 14 to produce a mark on the sensing portion 21 of the subject 2, wherein the mark can be a light spot, a pattern, a symbol, or a text. As such, a user of the liveness detecting device 1 is facilitated to know that the sensing portion 21 labeled with the mark is a body surface or a non-body surface.

On the other hand, FIG. 8 particularly depicts that the liveness detecting device 1 of the present invention can further comprise a lighting unit 15 and a driving unit 126. Accordingly, before the step S1 is executed, it is able to control the driving unit 126 so as to drive the lighting unit 15 project a detecting light to the sensing portion 21 of the subject 2, thereby making the diffuse light be radiated from the sensing portion 21. Furthermore, FIG. 9 depicts that the liveness detecting device 1 of the present invention simultaneously comprise the sensing portion labeling unit 14, the lighting unit 15 and the driving unit 126. Therefore, it is understood that, before the step S1 is executed, the lighting unit 15 can be controlled to project a detecting light to the sensing portion 21 of the subject 2, and the sensing portion labeling unit 14 is subsequently controlled to produce a mark on the sensing portion 21 of the subject 2.

After completing the step S1, the method flow is proceeded to step S2, so as to let a signal receiving unit 122 receive the diffuse light transmitted from the light sensing unit 11, and subsequently transmit a physiological signal to a signal processing unit 120. In which, the physiological signal is a photoplethysmography (PPG) signal. Next, in step S3, it is configured a physiological feature extracting unit to extract a first physiological feature from the physiological signal, or to extract a second physiological feature from the physiological signal that has been applied with at least one signal process.

In above descriptions, it is clearly explained that the first physiological features are a plurality of waveform features in the PPG signal. FIG. 5 shows a waveform diagram that depicts a photoplethysmography (PPG) signal, a velocity photoplethysmography (VPG) signal, and an acceleration photoplethysmography (APG) signal. In a practicable embodiment, the waveform features comprise: time interval of systolic wave, time interval of dicrotic wave, time interval of diastolic wave, existence of systolic notch in the systolic wave, existence of systolic peak in the systolic wave, existence of dicrotic notch in the dicrotic wave, existence of diastolic peak in the diastolic wave, waveform area of the systolic wave, waveform area of the dicrotic wave, waveform area of the diastolic wave, peak value of the systolic peak, peak value of the diastolic peak, slope of the dicrotic notch, time interval between two of the systolic notches, time interval between two of the systolic peaks, time interval between two of the dicrotic notches, time interval between two of the diastolic peaks, waveform area relativity between the diastolic wave and the dicrotic wave, peak value relativity between the systolic peak and the dicrotic notch, peak value relativity between the diastolic peak and the dicrotic notch.

On the other hand, above descriptions also explain that, after applying a first order differential process to the PPG signal, the physiological feature extracting unit 123 is able to extract several second physiological features from the VPG signal, including: first peak point (a1), first zero-crossing point (b1), first valley point (c1), second zero-crossing point (d1), second peak point (e1), second valley point (f1), time interval between any two of the forgoing points, and value relativity between any two of the forgoing points.

Furthermore, above descriptions also explain that, after applying a second order differential process to the PPG signal, the physiological feature extracting unit 123 is able to extract several second physiological features from the APG signal, including: early systolic positive wave, early systolic negative wave, late systolic re-increasing wave, late systolic re-decreasing wave, early diastolic positive wave, time interval between any two of the forgoing waves, and peak value relativity between any two of the forgoing waves.

On the other hand, it is noted that FIG. 7 depicts that the liveness detecting device 1 of the present invention can further comprise a physiological feature enhancing unit 125, which is provided in the signal processing module 12, and is coupled between the signal receiving unit 122 and the physiological feature extracting unit 123. Therefore, after completing the step (2) and before executing the step (3), a physiological feature enhancing unit 125 can be adopted for applying a physiological feature enhancing process to the physiological signal. Thus, after being applied with the physiological feature enhancing, the first physiological features such as systolic peak (point A in FIG. 5), dicrotic notch (point B in FIG. 5) and diastolic peak (point C in FIG. 5) contained in the PPG signal would therefore highlighted.

Consequently, the method flow is proceeded to step S4. In the step S4, a liveness detecting unit 124 that is coupled to the signal processing unit 120 and the physiological feature extracting unit 123, wherein the liveness detecting unit 124 is configured for determining whether the subject 2 is a living body or not according to the first physiological features and/or second physiological features. Moreover, the liveness detecting unit 124 is also able to determine whether the subject 2 is a living body or not based on the physiological data that is produced after the signal processing unit 120 completes at least one signal process of the physiological signal.

Therefore, through above descriptions, all embodiments and their constituting elements of the device and the method for liveness detection that are proposed by the present invention have been introduced completely and clearly. The above description is made on embodiments of the present invention. However, the embodiments are not intended to limit scope of the present invention, and all equivalent implementations or alterations within the spirit of the present invention still fall within the scope of the present invention.

What is claimed is:

1. A device for liveness detection, comprising:
   a light sensing unit, being used for facing a sensing portion of a subject, so as to collect a diffuse light from the sensing portion; and
   a signal processing module, comprising:
      a signal processing unit;
      a control unit, being coupled to the signal processing unit and the light sensing unit, so as to control the light sensing unit to collect the diffuse light from the sensing portion;
      a signal receiving unit, being coupled to the light sensing unit and the signal processing unit, so as to receive the diffuse light from the light sensing unit and subsequently transmit a physiological signal to the signal processing unit, such that the signal processing unit obtains at least one physiological data by applying at least one signal process to the physiological signal;
      a physiological feature extracting unit, being coupled to the signal receiving unit, and being configured for extracting a first physiological feature from the physiological signal, or extracting a second physiological feature from the physiological signal that has been applied with at least one signal process; and
      a liveness detecting unit, being coupled the signal processing unit and the physiological feature extracting unit;
   wherein the liveness detecting unit is configured for determining whether the subject is a living body or not according to the first physiological features and/or second physiological features;
   wherein the liveness detecting unit is also able to determine whether the subject is a living body or not based on the physiological data received from the signal processing unit.

2. The device of claim 1, wherein the physiological data comprises at least one physiological index that is selected from the group consisting of blood volume, heart rate, respiratory rate, arterial oxygen saturation, blood pressure, blood vessel viscosity, venous function, venous reflux, ankle pressure, genital response, and cardiac output.

3. The device of claim 1, further comprising:
   a data outputting unit, being coupled to the signal processing unit, thereby facilitating the signal processing unit output the physiological data.

4. The device of claim 1, wherein the physiological signal is a photoplethysmography (PPG) signal, and the first physiological features are selected from the group consisting of a plurality of waveform features in the PPG signal, at least one waveform feature for describing arterial oxygen extracted from the PPG signal, at least one waveform feature for describing blood pressure extracted from the PPG signal, and at least one waveform feature for describing respiratory extracted from the PPG signal.

5. The device of claim 1, wherein the physiological signal is a photoplethysmography (PPG) signal, and the physiological signal that has been applied with the signal process is selected from the group consisting of first derivative PPG signal, second derivative PPG signal, third derivative PPG signal, fourth derivative PPG signal, and filtering process.

6. The device of claim 1, wherein the physiological signal is further processed to a derivative photoplethysmography (PPG) signal that is selected from the group consisting of first derivative PPG signal, second derivative PPG signal, third derivative PPG signal, and fourth derivative PPG signal, and the second physiological features are extracted from the forgoing derivative PPG signal; the second physiological features being selected from the group consisting of a plurality of waveform features in the derivative PPG signal, at least one waveform feature for describing arterial oxygen extracted from the derivative PPG signal, at least one waveform feature for describing blood pressure extracted from the derivative PPG signal, and at least one waveform feature for describing respiratory extracted from the derivative PPG signal.

7. The device of claim 1, further comprising:
a sensing portion labeling unit, being controlled by the control unit for producing a mark on the sensing portion of the subject;
wherein the sensing portion is a body surface of the subject, and the mark being selected from the group consisting of light spot, pattern, symbol, and text.

8. The device of claim 4, further comprising:
a physiological feature enhancing unit, being coupled between the signal receiving unit and the physiological feature extracting unit, and being used for applying a physiological feature enhancing process to the physiological signal before the physiological feature extracting unit receives the physiological signal.

9. The device of claim 4, wherein the plurality of waveform features in the PPG signal comprise: time interval of systolic wave, time interval of dicrotic wave, time interval of diastolic wave, existence of systolic notch in the forgoing systolic wave, existence of systolic peak in the forgoing systolic wave, existence of dicrotic notch in the forgoing dicrotic wave, existence of diastolic peak in the forgoing diastolic wave, waveform area of the forgoing systolic wave, waveform area of the forgoing dicrotic wave, waveform area of the forgoing diastolic wave, peak value of the forgoing systolic peak, peak value of the forgoing diastolic peak, slope of the forgoing dicrotic notch, time interval between two of the forgoing systolic notches, time interval between two of the forgoing systolic peaks, time interval between two of the forgoing dicrotic notches, time interval between two of the forgoing diastolic peaks, waveform area relativity between the forgoing diastolic wave and the forgoing dicrotic wave, peak value relativity between the forgoing systolic peak and the forgoing dicrotic notch, peak value relativity between the forgoing diastolic peak and the forgoing dicrotic notch.

10. The device of claim 6, wherein the plurality of waveform features in the PPG signal comprise: a first peak point, a first zero-crossing point, a first valley point, a second zero-crossing point, a second peak point, a second valley point, time interval between any two of the forgoing points, value relativity between any two of the forgoing points.

11. The device of claim 6, wherein the plurality of waveform features comprise: early systolic positive wave, early systolic negative wave, late systolic re-increasing wave, late systolic re-decreasing wave, early diastolic positive wave, time interval between any two of the forgoing waves, and peak value relativity between any two of the forgoing waves.

12. The device of claim 1, wherein the diffuse light is radiated from the sensing portion in case of the subject is exposed under an ambient light, and the ambient light being selected from the group consisting of natural light and artificial light.

13. The device of claim 1, further comprising:
a lighting unit; and
a driving unit, being provided in the signal processing module, and being coupled to control unit and the lighting unit;
wherein the driving unit is controlled by the control unit, so as to drive the lighting unit project a detecting light to the sensing portion of the subject, thereby making the diffuse light be radiated from the sensing portion.

14. A method for liveness detection, comprising following steps:
(1) using a light sensing unit to collect a diffuse light that is radiated from a sensing portion of a subject;
(2) letting a signal receiving unit receive the diffuse light transmitted from the light sensing unit, and subsequently transmit a physiological signal to a signal processing unit;
(3) configuring a physiological feature extracting unit to extract a first physiological feature from the physiological signal, or to extract a second physiological feature from the physiological signal that has been applied with at least one signal process; and
(4) providing a liveness detecting unit coupled to the signal processing unit and the physiological feature extracting unit, wherein the liveness detecting unit is configured for determining whether the subject is a living body or not according to the first physiological features and/or second physiological features; wherein the liveness detecting unit is also able to determine whether the subject is a living body or not based on the physiological data that is produced after the signal processing unit completes at least one signal process of the physiological signal.

15. The method of claim 14, wherein after completing the step (2) and before executing the step (3), a physiological feature enhancing unit being provided to be coupled between the signal receiving unit and the physiological feature extracting unit, thereby applying a physiological feature enhancing process to the physiological signal.

16. The method of claim 14, wherein the physiological data comprises at least one physiological index that is selected from the group consisting of blood volume, heart rate, respiratory rate, arterial oxygen saturation, blood pressure, blood vessel viscosity, venous function, venous reflux, ankle pressure, genital response, and cardiac output.

17. The method of claim 14, wherein the physiological signal is a photoplethysmography (PPG) signal, and the first physiological features are selected from the group consisting of a plurality of waveform features in the PPG signal, at least one waveform feature for describing arterial oxygen extracted from the PPG signal, at least one waveform feature for describing blood pressure extracted from the PPG signal, and at least one waveform feature for describing respiratory extracted from the PPG signal.

18. The method of claim 14, wherein the physiological signal is a photoplethysmography (PPG) signal, and the physiological signal that has been applied with the signal process is selected from the group consisting of first derivative PPG signal, second derivative PPG signal, third derivative PPG signal, and fourth derivative PPG signal.

19. The method of claim 18, wherein the physiological signal is further processed to a derivative photoplethysmography (PPG) signal that is selected from the group consisting of first derivative PPG signal, second derivative PPG signal, third derivative PPG signal, and fourth derivative PPG signal, and the second physiological features are extracted from the forgoing derivative PPG signal; the second physiological features being selected from the group consisting of a plurality of waveform features in the derivative PPG signal, at least one waveform feature for describing arterial oxygen extracted from the derivative PPG signal, at least one waveform feature for describing blood pressure extracted from the derivative PPG signal, and at least one waveform feature for describing respiratory extracted from the derivative PPG signal.

* * * * *